United States Patent [19]

Nishida et al.

[11] Patent Number: 5,711,937
[45] Date of Patent: Jan. 27, 1998

[54] ORAL COMPOSITION

[75] Inventors: Yasukuni Nishida; Midori Morishima; Maimi Ohta, all of Odawara; Tetsuo Gomi, Tokyo; Yoshihiro Harada, Odawara, all of Japan

[73] Assignee: Lion Corporation, Tokyo, Japan

[21] Appl. No.: 571,914

[22] PCT Filed: Jun. 24, 1994

[86] PCT No.: PCT/JP94/01019

§ 371 Date: Dec. 27, 1995

§ 102(e) Date: Dec. 27, 1995

[87] PCT Pub. No.: WO95/00110

PCT Pub. Date: Jan. 5, 1995

[30] Foreign Application Priority Data

Jun. 28, 1993 [JP] Japan ............... 5-181970
Dec. 24, 1993 [JP] Japan ............... 5-348108

[51] Int. Cl.⁶ .................. A61K 7/16; A61K 7/26; A61K 7/28
[52] U.S. Cl. ................. 424/49; 424/50; 424/58
[58] Field of Search ................. 424/49–58

[56] References Cited

FOREIGN PATENT DOCUMENTS

| | | |
|---|---|---|
| 60-142915 | 7/1985 | Japan. |
| 61-112029 | 5/1986 | Japan. |
| 61-277632 | 12/1986 | Japan. |
| 3-52999 | 3/1991 | Japan. |
| 3-115213 | 5/1991 | Japan. |

*Primary Examiner*—Shep K. Rose
*Attorney, Agent, or Firm*—Birch, Stewart, Kolasch & Birch, LLP

[57] ABSTRACT

An oral composition is provided which is improved in antibody stability so that the antibody may satisfactorily exert its effect after long-term storage and has a pleasant feel on use. A flavor component selected from the group consisting of carvone, anethole, cineole, methyl salicylate, eugenol, ethyl butyrate, and cinnamic aldehyde, and l-menthol are blended in a weight ratio of from 1:9 to 8:2 in an oral composition containing an antibody selected from the group consisting of a serum antibody, egg yolk antibody and milk antibody.

10 Claims, No Drawings

ORAL COMPOSITION

This is a 371 PCT/JP94/01019 filed Jun. 24, 1994.

FIELD OF THE INVENTION

This invention relates to an oral composition containing an antibody which is effective for the prevention or treatment of dental caries and peridontal diseases and more particularly, to such an oral composition which allows the antibody to exert its effect satisfactorily even after long-term shelf storage and presents a pleasant feel on use.

BACKGROUND OF THE INVENTION

Research has been done in the past to blend an antibody in dentifrices and other oral compositions as an active ingredient for preventing dental caries, the antibody having specific interaction with *Streptococcus mutans* bacterium and being effective for prohibiting adhesion of the bacterium to the dental surface and formation of dental plaque.

Research has also been done to blend an antibody in dentifrices and other oral compositions as an active ingredient for preventing periodontal diseases, the antibody having specific interaction with periodontal disease associated bacteria and being effective for suppressing colonization of the bacteria in the oral cavity.

However, there is a problem that the above-mentioned antibodies tend to be deactivated under the influence of anionic surfactants in the oral compositions. Thus, various studies have been made on the technique for blending antibodies in a stable manner.

Additionally the oral compositions must have a pleasant feel on use since they are used in the oral cavity. Therefore, various flavor components must be blended to improve the feel on use depending on a particular type of consumers' favorite taste or the like although there arises a problem that many flavor components have undesirable influence on the stability of antibodies.

Therefore, it is desired to develop an oral composition which is improved in antibody stability and feel on use.

DISCLOSURE OF THE INVENTION

An object of the present invention is to provide an antibody-containing oral composition which is improved in antibody stability, allows the antibody to exert its effect satisfactorily even after long-term shelf storage and presents a pleasant feel on use.

Making extensive investigations to attain the above object, the inventors have found that by using a flavor component selected from the group consisting of carvone, anethole, cineole, methyl salicylate, eugenol, ethyl butyrate, and cinnamic aldehyde, and 1-menthol in combination in a weight ratio of from 1:9 to 8:2 in an oral composition containing an antibody selected from the group consisting of a serum antibody, egg yolk antibody and milk antibody, quite unexpectedly, there is obtained an oral composition which maintains the antibody stable and even after long-term shelf storage, allows the antibody to retain its activity satisfactorily and to fully exert its effect, and provides a pleasant feel on use. The present invention is predicated on this finding.

Therefore, the present invention provides an oral composition characterized in that a flavor component selected from the group consisting of carvone, anethole, cineole, methyl salicylate, eugenol, ethyl butyrate, and cinnamic aldehyde, and 1-menthol are blended in a weight ratio of from 1:9 to 8:2 in an oral composition containing an antibody selected from the group consisting of a serum antibody, egg yolk antibody and milk antibody.

The oral composition of the invention is prepared as dentifrices including toothpaste, wet toothpowder, toothpowder, and liquid dentifrice, liquid mouth refreshers such as mouthwash, solid mouth refreshers such as troche, chewing gum, and the like. The composition contains an antibody selected from the group consisting of serum antibodies, egg yolk antibodies and milk antibodies as an active ingredient and further contains a flavor component selected from the group consisting of carvone, anethole, cineole, methyl salicylate, eugenol, ethyl butyrate, and cinnamic aldehyde, and 1-menthol combined in a weight ratio of from 1:9 to 8:2.

The antibody used herein may be any of the antibodies corresponding to various antigens. For example, antibodies corresponding to various antigens of dental cariogenic bacteria may be used. There may be used an antibody against *Streptococcus mutans* bacterium as a dental cariogenic bacterium.

There may also be used antibodies corresponding to various antigens of periodontal disease associated bacteria. The periodontal disease associated bacteria are ones which are generally considered as having close etiological relation with the periodontal diseases and include, for example, *Actinobacillus actinomycetemcomitans*, *Porphyromonas gingivalis*, *Actinomyces viscosus*, *Prevotella intermedia*, *Fusobacterium nucleatum*, species of Capnocytophaga, *Eikenella corrodens*, *Campylobacter rectus*, *Bacteroides forsythus*, spirochetes such as of *Treponema denticola* and the like.

The antibody used herein may be selected from serum antibodies or milk antibodies obtained by using antigens of the above-mentioned dental cariogenic bacteria and periodontal disease associated bacteria in the form of whole cell, fimbriae, capsule, bacterial cell extract or bacterial surface layer polysaccharide and immunizing mammals therewith, or egg yolk antibodies obtained by immunizing fowls with the antigens. Monoclonal antibodies prepared by well-known methods are also acceptable.

The method of preparing the antibody, more particularly the method of immunizing animals, method of purifying the antibody and the like may be conventional methods. Note that illustrative examples of preparation are described later as Reference Examples.

In the oral composition of the invention, either a single antibody may be blended or two or more antibodies may be used in combination. The amount of antibody blended is not particularly limited although the oral composition generally contains 0.0001 to 10% (% by weight throughout the specification), preferably 0.002 to 5% of the antibody.

According to the invention, one or more members selected from carvone, anethole, cineole, methyl salicylate, eugenol, ethyl butyrate, and cinnamic aldehyde are blended in the antibody-containing oral composition, although anethole is preferably used among others.

The flavor components may be blended in isolated form although essential oils containing a flavor component may also be blended, for example, spearmint oil in the case of carvone.

Further, 1-menthol which is used along with the flavor component may be blended in isolated form although essential oils containing the same, for example, peppermint (Mentha piperita) oil and/or cornmint (Mentha arvensis) oil may also be blended.

The proportion of the flavor component and l-menthol blended is from 1:9 to 8:2, preferably from 2:8 to 7:3 in weight ratio because blending within this proportional range insured stable blending of the antibody and improves feel on use by providing an appropriate combination of refreshingness, body and pungent taste. On the contrary, if the proportion of the flavor component blended is smaller than the above-defined range, the body and pungent taste become short and the feel on use deteriorates, and if the proportion of the flavor component is larger than the above-defined range, the antibody lowers in stability and refreshingness becomes short, failing to achieve the object of the invention.

Also, the amount of the flavor component blended is desirably 0.01 to 0.5% of the entire composition. The feel on use will deteriorate with less than 0.01% of the flavor component whereas the antibody stability and feel on use will lower with more than 0.5% of the flavor component.

Further, it is desired in the present invention that the total amount of the flavor component and l-menthol blended be 0.1 to 5%, especially 0.3 to 3% of the entire composition. The body and refreshingness become short with a total blending amount of less than 0.1% whereas the pungent taste becomes too strong with a total blending amount of more than 5%, and the antibody stability is not further improved when more amounts are blended.

In addition to the antibody, the oral composition of the invention may have another active ingredient blended therein, for example, enzymes such as dextranase, amylase, protease, mutanase, lysozyme, and lytic enzyme; bactericides such as chlorhexidines, triclosan, and cetyl pyridinium chloride; fluorides such as alkali metal monofluorophosphates, sodium fluoride and stannous fluoride; as well as stannous compounds, epsilon-aminocaproic acid, tranexamic acid, allantoin, aluminum chlorohydroxyallantoin, dihydrocholesterol, glycyrrhizin salts, azulene, vitamin E, sodium chloride, and water-soluble inorganic phosphoric acid compounds. It is especially desired to use alkali metal monofluorophosphates such as sodium monofluorophosphate along with the antibody because the antibody becomes more stable and the retentivity of the antibody after long-term shelf storage can be kept high. In this regard, the amount of alkali metal monofluorophosphate added is preferably 10 to 10,000 ppm calculated as fluorine. Examples of the water-soluble inorganic phosphoric acid compound include potassium and sodium salts of orthophosphoric acid, pyrophosphoric acid, and polyphosphoric acid, with the potassium salts of these phosphoric acids being especially preferred.

In addition to the flavor component, any other flavor components such as aliphatic alcohols having 7 to 17 carbon atoms and esters thereof, terpene hydrocarbons, phenol ethers, aldehydes, ketones and lactones and essential oils may be blended insofar as the benefits of the invention are not adversely affected.

In the composition of the invention, any other components commonly used may be blended in accordance with a particular type of composition. For example, in the case of dentifrices, one or more of aluminum oxide, aluminum hydroxide, calcium hydrogen phosphate dihydrate or anhydride, silica gel, zirconosilicate, silicic anhydride, aluminosilicate, calcium carbonate, calcium pyrophosphate, aluminum silicate, insoluble sodium metaphosphate, magnesium tertiary phosphate, magnesium carbonate, calcium sulfate, and synthetic resins may be blended as an abrasive generally in an amount of 20 to 90% of the entire composition, especially in an amount of 20 to 60% in the case of toothpaste. It is preferred in the invention to use silica series compounds as a main abrasive because the antibody and dentifrice itself are further improved in stability. The silica series compounds include precipitated silica, silica gel, aluminosilicate, and zirconosilicate with a particle size of 1 to 30 µm being preferred from the aspect of use.

Further, in the dentifrice composition, carrageenan, sodium carboxymethyl cellulose, alkali metal alginates such as sodium alginate, gums, polyvinyl alcohol, vee gum or the like may be blended (conventional blending amount 0.3 to 5%). When an alkali metal monofluorophosphate is blended as an active ingredient, a combined use of carrageenan and alkali metal alginate is desirable from the points of view of stability and feel on use of the composition. Since kappa-carrageenan (κ-carrageenan) is more effective for preventing texture roughening of the dentifrice composition than conventional carrageenan (kappa and iota mixture), κ-carrageenan is the preferred carrageenan used herein.

Furthermore, sorbitol, glycerin, propylene glycol, 1,3-butylene glycol, polyethylene glycol, xylitol, maltitol, lactitol, or the like may be blended as a humectant (conventional blending amount 10 to 70%). It is preferred to use propylene glycol as a liquid humectant dispersion. Since the retentivity of the antibody after storage is reduced by blending a large amount of propylene glycol, it is desirable to blend sorbitol as a main humectant and use propylene glycol in admixture therewith.

Moreover, there may be blended anionic surfactants such as sodium lauryl sulfate, sodium lauroyl sarcosinate, α-olefin sulfonate, taurate, lauryl monoglyceride sulfate and lauryl monoglyceride sulfonate, and soap; nonionic surfactants such as lauroyl diethanol amide, stearyl monoglyceride, sucrose fatty acid esters, lactose fatty acid esters, lactitol fatty acid esters, maltitol fatty acid esters, and polyoxyethylene sorbitan monostearate; ampholytic surfactants such as betain and amino acid type surfactants (conventional blending amount 0.5 to 7%); sweeteners such as saccharin sodium, stevioside, neohesperidyl dihydrochalcone, taumatine, glycyrrhizin, and perillartine; preservatives such as parahydroxybenzoates and sodium benzoate; and components such as gelatin and peptone.

A toothpaste may be prepared by kneading the above-mentioned components with an appropriate amount of water. The thus obtained toothpaste composition is used after it is filled in appropriate containers, for example, aluminum tubes, laminate tubes having aluminum foil laminated with plastic material on either surface, plastic tubes, bottles and aerosol containers.

Oral compositions other than the toothpaste may be prepared by conventional methods using a commonly used base material.

The oral composition of the invention allows the serum antibodies, egg yolk antibodies and milk antibodies to be stably retained and to fully exert their effect over a long term, permits a choice of a flavor component from a wise variety, and provides a pleasant feel on use.

Examples and Comparative Examples are given below by way of illustration of the present invention although the present invention is not limited to these Examples.

In the examples, all percents are by weight.
Antibody preparation process A

An antigen was first prepared by the following procedure.
(1) Preparation of PAc antigen PAc antigen was prepared according to the method of Lehner (J. General Microbiology, 122, 217–225, 1981) by growing S. mutans 10449 in 20 liters of TPY dialysis medium, centrifuging the medium, fractionating the resulting supernatant with 60% ammonium sulfate, and collecting the precipitate. The precipitate was dissolved in 10 mM tris-hydrochloric acid buffer solution (pH 7.5), dialyzed with the buffer solution, adsorbed to DEAE-Sephacel column chromatograph, and eluted in accordance with a NaCl concentration gradient. The end fraction was then concentrated and purified by gel filtration through Sepharose 6B.

(2) Preparation of bacterial whole cell

S. mutans 10449 was grown for 18 hours in 20 liters of TTY medium under aerobic conditions at 37° C. The culture medium was centrifuged at 8,000 rpm for 20 minutes, and culture supernatant was removed. The bacteria were collected, washed three times with phosphate buffered saline (PBS), further washed three times with sterilized distilled water, and freeze dried.

(3) Preparation of bacterial cell coupled glucosyltransferase (GTF)

S. mutans 10449 was grown for 18 hours in 20 liters of TTY medium under aerobic conditions at 37° C. The culture medium was centrifuged at 8,000 rpm for 20 minutes and culture supernatant was removed. The bacteria were collected, washed three times with physiological saline, and extracted with a solution containing 4M urea and 0.5M sodium chloride at room temperature for one hour with slow occasional stirring. After centrifugation (8,000 rpm, 20 minutes), the required liquid phase was dialyzed with 10 mM phosphate buffered saline (pH 6.0). After the precipitate was removed by centrifugation, the supernatant was treated with 60% saturated ammonium sulfate, and the resulting precipitate was collected under the above-mentioned centrifugation. The precipitate was dissolved in the above-mentioned buffer solution and dialyzed with the buffer solution. After the precipitate was centrifugally removed from the dialyzate, the supernatant was sterilized through a 0.22-μm membrane filter, obtaining an antigen for immunization.

(4) Preparation of water-soluble glucan synthetic enzyme (GTF-S)

S. mutans 10449 was grown for 18 hours in 20 liters of TTY medium under aerobic conditions at 37° C. The culture medium was centrifuged at 8,000 rpm for 20 minutes, and the bacterial cell was removed. The supernatant was treated with 55% saturated ammonium sulfate and the resulting precipitate was centrifuged, and supernatant was discarded. Then the precipitate was dissolved in a histidine-HCl buffer solution (pH 6.0) and dialyzed with the same buffer. The precipitate was centrifugally removed and the supernatant was sterilized through a 0.22-μm membrane filter and passed through a Polybuffer PBE 94 column (manufactured by Pharmacia) of 2.5×25 cm. The fractions adsorbed in the column were selectively eluted in accordance with a pH gradient using Polybuffer 74 (manufactured by Pharmacia). A fraction at pH 5.5–4.9 was found to have high GTF activity. This fraction was collected and treated with 80% saturated ammonium sulfate, obtaining a precipitate. The precipitate was dissolved in a 10 mM phosphate buffered saline (pH 6.0) and dialyzed with the same buffer. The precipitate was removed by centrifugation and the supernatant was used as an antigen.

It is to be noted that GTF activity was determined by mixing 10 μl of sample as a substrate with 10 μl of 0.2M phosphate buffered saline (pH 6.0) containing 20 mM [$^{14}$C-glucose] sucrose (0.05 ci/mol), allowing reaction to incubate for one hour, spotting the small aliquot amount of reaction mixture on a paper filter (1×1 cm), washing it with methanol, measuring the quantity of radioactivity taken in the methanol-insoluble glucan remaining on the paper filter, and calculating GTF activity therefrom, with the activity capable of converting 1 μmol of glucose into glucan within one minute per unit.

Next, a hen egg yolk antibody, serum antibody and milk antibody corresponding to each of the above-prepared antigens were prepared by the following methods.

(1) Preparation of hen egg yolk antibody

A W/O type emulsion was prepared by mixing 0.5 ml of a solution containing 1 mg/ml of the antigen and 0.5 ml of Freund's incomplete adjuvant (FIA) in a ratio of 1:1. A hen was initially immunized by injecting the emulsion into the left and right pectral muscles, 0.5 ml each, and successively immunized at intervals of one week, and eggs were collected from the end of one month. While appropriate immunization was repeated upon detecting lowered antibody titer, eggs were collected over about one year. To the egg yolk separated from eggs were added an equal volume of water and further an equal volume of a 0.5% γ-carrageenan suspension. After stirring, the mixture was centrifuged at 8,000 rpm for 20 minutes to provide a supernatant, which was an antibody-containing water soluble fraction (WSF) and was measured for antibody titer before use. The foregoing procedure yielded 10 ml of a liquid containing 80 to 320 unit/ml (1 mg/ml) of hen egg yolk antibody.

(2) Preparation of milk antibody

The antigen was diluted to a concentration of 50 μg/ml to 200 mg/ml and mixed with an equal volume of Freund's incomplete adjuvant. Pregnant goat, rabbit, cow and horse were immunized by subcutaneous injection on their back in an amount of 0.3 ml per body and thereafter immunized three times with the mixture of the antigen and Freund's incomplete adjuvant at intervals of 2 to 4 weeks. After parturition, the colostrum was collected. The colostrial sample was combined with an equal volume of 0.9% saline and centrifuged at 1,200 rpm for 60 minutes. With the upper layer of fat and the precipitate removed, the intermediate liquid component was collected and adjusted to pH 4 by adding conc. hydrochloric acid. The liquid was further centrifuged at 5,000 rpm for 30 minutes. After the supernatant was neutralized with trishydroxyaminomethane, ammonium sulfate was added to the supernatant to 75% saturation, from which a precipitate was collected. The precipitate was dialyzed with phosphate buffered saline, obtaining a milk antibody component (endo-liquid). There was obtained a liquid containing 10 to 20 unit/ml (1 mg/ml) of colostrial antibody.

(3) Preparation of serum antibody

After 4 times of immunization in the same manner as described above, blood was collected, clotted and centrifuged, with the supernatant being used as a sample. Ammonium sulfate was added to this antiserum to 50% saturation, from which a precipitate was collected, dialyzed with phosphate buffered saline, obtaining a serum antibody (endo-liquid). There was obtained a liquid containing about 80 to 320 unit/ml (1 mg/ml) of serum antibody.

Note that each of the above-prepared antibodies was measured for antibody titer by the following procedure using a bacterial agglutination test.

Antibody titer measurement (1) Bacterial suspension

One or two colonies of S. mutans 10449 on TYC agar medium were inoculated into 200 ml of BHI medium and anaerobically incubated at 37° C. for 18 hours. The bacteria were collected and washed three times with physiological saline (BSA physiological saline) containing 0.1% bovine serum albumin. The bacteria as washed were suspended in BSA physiological saline and adjusted to $OD_{550nm}$ 1.0. The bacterial suspension was prepared on demand.

(2) Sample antibody

Samples were prepared by diluting each antibody 20, 30, 50, 70 and 90 times respectively, and then each was diluted by a factor of $2^n$.

(3) Manipulation

On a micro-plate 50 µl of the dilute antibody and 50 µm of the bacterial suspension were mixed and agitated and thereafter allowed to stand 3 hours at 37° C. and then overnight at 4° C.

(4) Detection of bacterial agglutination

On inspection of the micro-plate bottom at the end of overnight rest, agglutination was judged positive when no bacterial spots developed and negative when even a few spots were observed.

EXAMPLES 1–9 & COMPARATIVE EXAMPLES 1–2

Toothpaste compositions of the formulation shown in Table 1 and Table 2 were prepared. Immediately after preparation and after shelf storage at 40° C. for one month, the antibody quantity was measured by an ELISA method using an immunogen, determining the antibody retentivity. The result is expressed as the residual activity equal to the quantity after 40° C. storage divided by the quantity immediately after blending which is 100%. The toothpaste compositions were also evaluated for feel on use by a sensory test using a special panel. The results are shown in Table 1 and Table 2.

TABLE 1

| Dentifrice composition component | Comparative Example 1 | Example 1 | Example 2 | Example 3 | Comparative Example 3 |
|---|---|---|---|---|---|
| Anethole/l-menthol | 1:20 | 1:9 | 5:5 | 8:2 | 9:1 |
| Silicic anhydride | 20% | 20% | 20% | 20% | 20% |
| Glycerin | 30 | 30 | 30 | 30 | 20 |
| Sorbitol | 20 | 20 | 20 | 20 | 20 |
| Sodium carboxymethyl cellulose | 1.0 | 1.0 | 1.0 | 1.0 | 1.0 |
| Sodium lauryl sulfate | 1.2 | 1.2 | 1.2 | 1.2 | 1.2 |
| Lauroyl diethanolamide | 1.0 | 1.0 | 1.0 | 1.0 | 1.0 |
| Gelatin | 1.0 | 1.0 | 1.0 | 1.0 | 1.0 |
| Anethole | 0.05 | 0.1 | 0.5 | 0.4 | 0.45 |
| l-menthol | 1.0 | 0.9 | 0.5 | 0.1 | 0.05 |
| Saccharin | 0.1 | 0.1 | 1.0 | 1.0 | 1.0 |
| Orange oil | 0.05 | 0.05 | 0.05 | 0.05 | 0.05 |
| Benzaldehyde | 0.02 | 0.02 | 0.02 | 0.02 | 0.02 |
| Sodium fluoride | 0.5 | 0.5 | 0.5 | 0.5 | 0.5 |
| Anti-PAc horse serum antibody | 0.2 | 0.2 | 0.2 | 0.2 | 0.2 |
| Water | balance | balance | balance | balance | balance |
| Total | 100.00 | 100.00 | 100.00 | 100.00 | 100.00 |
| Antibody retentivity (40° C./1 month storage) | Δ | ○ | ○ | ○ | Δ |
| Feel on use | X | ○ | ○ | ○ | V |

Antibody retentivity evaluation criterion
○: retentivity 70% or more
Δ: retentivity 30% to less than 70%
X: residual quantity less than 30%
Feel on use evaluation criterion
○: pleasant
X: monotonous flavor, unpleasant feel
V: short refreshing, unpleasant feel

TABLE 2

| Dentifrice composition component | Example 4 | Example 5 | Example 6 | Example 7 | Example 8 | Example 9 |
|---|---|---|---|---|---|---|
| Silicic anhydride | 20% | 20% | 20% | 20% | 20% | 20% |
| Glycerin | 30 | 30 | 30 | 30 | 30 | 30 |
| Sorbitol | 20 | 20 | 20 | 20 | 20 | 20 |
| Sodium carboxymethyl cellulose | 1.0 | 1.0 | 1.0 | 1.0 | 1.0 | 1.0 |
| Sodium lauryl sulfate | 1.2 | 1.2 | 1.2 | 1.2 | 1.2 | 1.2 |
| Lauroyl diethanolamide | 1.0 | 1.0 | 1.0 | 1.0 | 1.0 | 1.0 |
| Gelatin | 1.0 | 1.0 | 1.0 | 1.0 | 1.0 | 1.0 |
| Carvone | 0.4 | — | — | — | — | — |
| Cineole | — | 0.3 | — | — | — | — |
| Methyl salicylate | — | — | 0.5 | — | — | — |
| Eugenol | — | — | — | 0.1 | — | — |
| Ethyl butyrate | — | — | — | — | 0.1 | — |
| Cinnamic aldehyde | — | — | — | — | — | 0.3 |
| l-menthol | 0.5 | 0.5 | 0.5 | 0.5 | 0.5 | 0.5 |
| Saccharin | 0.1 | 0.1 | 0.1 | 0.1 | 0.1 | 0.1 |
| Orange oil | 0.05 | 0.05 | 0.05 | 0.05 | 0.05 | 0.05 |
| Benzaldehyde | 0.02 | 0.02 | 0.02 | 0.02 | 0.02 | 0.02 |
| Sodium fluoride | 0.5 | 0.5 | 0.5 | 0.5 | 0.5 | 0.5 |
| Anti-PAc horse serum antibody | 0.2 | 0.2 | 0.2 | 0.2 | 0.2 | 0.2 |
| Water | balance | balance | balance | balance | balance | balance |
| Total | 100.00 | 100.00 | 100.00 | 100.00 | 100.00 | 100.00 |
| Antibody retentivity (40° C./1 month storage) | ○ | ○ | ○ | ○ | ○ | ○ |
| Feel on use | ○ | ○ | ○ | ○ | ○ | ○ |

Antibody preparation process B

Antigens were prepared by the following processes.

(1) Preparation of *Porphyromonas gingivalis* whole cell antigen

*Porphyromonas gingivalis* 381 (FERM BP-1027) was inoculated in TODD HEWITT broth supplemented with hemin and menadione, and grown for two days. The bacteria were collected, washed with PBS (phosphate buffered saline, pH 7.4) and treated with 0.5% formalin overnight, washed three times with PBS, and then obtained whole cell antigen.

(2) Preparation of *Porphyromonas gingivalis* fimbrial antigen

*Porphyromonas gingivalis* 381 grown for two days were collected and washed in the same manner as above, slowly agitated for two days in PBS together with glass beads, and passed through an injection needle (No. 25) three times for separating fimbriae from the bacterial cell. The supernatant was separated by centrifugation at 8,000 rpm for 15 minutes, dialyzed, and freeze dried, obtaining a fimbrial antigen.

(3) Preparation of *Porphyromonas gingivalis* capsular antigen

The bacteria collected in the same manner as above were suspended in PBS containing 0.01M EDTA, allowed for reaction at 60° C. for 30 minutes, and passed through an injection needle three times for separating capsule from the bacterial cell. Then the bacterial cell was separated by centrifugation at 8,000 rpm for 15 minutes, and the supernatant was subjected to ultracentrifugation at 40,000 rpm for 2 hours, obtaining a sedimented residue as a capsular antigen.

(4) Preparation of *Actinobacillus actinomycetemcomitans* bacterial surface layer polysaccharide antigen

*Actinobacillus actinomycetemcomitans* Y4 (ATCC 43718) was inoculated in TODD HEWITT broth supplimented with 1% yeast extract and grown for 3 days at 37° C. in an incubator containing 5% $CO_2$. The bacteria were collected, washed three times with saline, suspended in saline, and autoclaved at 121° C. for 15 minutes. After cooling, the supernatant was collected by centrifugation at 10,000×g for 20 minutes whereupon saline was added to the sedimented residue again and the above-mentioned extraction procedure was repeated. The combined supernatant was dialyzed extensively against distilled water and freeze dried, obtaining a bacterial surface layer polysaccharide antigen.

Next, a hen egg yolk antibody, serum antibody and milk antibody corresponding to each of the above-prepared antigens were prepared.

(1) Preparation of hen egg yolk antibody

A W/O type emulsion was prepared by mixing 0.5 ml of a solution containing 1 mg/ml of the antigen and 0.5 ml of Freund's incomplete adjuvant (FIA) in a ratio of 1:1. A hen was initially immunized by injecting the emulsion into the left and right pectral muscles, 0.5 ml each, and successively immunized at intervals of one week, and eggs were collected from the end of one month. While appropriate immunization was repeated upon detecting lowered antibody titer, eggs were collected over about one year. To the egg yolk separated from eggs were added an equal volume of water and further an equal volume of a 0.5% γ-carrageenan suspension. After stirring, the mixture was centrifuged at 8,000 rpm for 20 minutes to provide a supernatant, which was a hen egg yolk antibody sample.

(2) Preparation of serum antibody

The antigen was diluted to a concentration of 50 µg/ml to 200 mg/ml and mixed with an equal volume of Freund's incomplete adjuvant. A goat, rabbit, cow, horse and sheep were immunized by subcutaneous injection on their back in an amount of 0.3 ml per body and thereafter immunized three times with the mixture of the antigen and Freund's incomplete adjuvant at intervals of 2 to 4 weeks. Thereafter, blood was collected, clotted and centrifuged, with the supernatant being used as an antiserum sample. Ammonium sulfate was added to this antiserum to 50% saturation, from which a precipitate was collected, dialyzed against PBS, obtaining a serum antibody sample.

(3) Preparation of milk antibody

A pregnant goat, cow and sheep were subjected to 4 times of immunization in the same manner as described above. After parturition, the colostrum was sampled. The colostral sample was combined with an equal volume of saline and centrifuged at 1,200 rpm for 60 minutes. With the upper layer of fat and the precipitate removed, the intermediate liquid component was collected and adjusted to pH 4 by adding conc. hydrochloric acid. The liquid was further centrifuged at 5,000 rpm for 30 minutes. After the supernatant was neutralized with tris(hydroxymethyl) aminomethane, ammonium sulfate was added to the supernatant to 75% saturation, from which a precipitate was collected. The precipitate was dialyzed against PBS, obtaining a milk antibody sample.

EXAMPLES 10–18 & COMPARATIVE EXAMPLES 3–4

Toothpaste compositions of the formulation shown in Tables 3 and 4 were prepared. Immediately after preparation and after shelf storage at 40° C. for one month, the antibody quantity was measured by an ELISA method using an immunogen, determining the antibody retentivity. The results is expressed as the residual activity equal to the quantity after 40° C. storage divided by the quantity immediately after blending which is 100%. The toothpaste compositions were also evaluated for feel on use by a sensory test using a special panel. The results are shown in Tables 3 and 4. It is to be noted that all the blending amounts (%) in the examples are % by weight. Also note that Aa is *Actinobacillus actinomycetemcomitans*, Pg is *Porphyromonas gingivalis*, Av is *Actinomyces viscosus*, Pi is *Prevotella intermedia*, Fn is *Fusobacterium nucleatum*, Cr is *Campylobacter rectus*, Bf is *Bacteroides forsythus*, and Td is *Treponema denticola*.

TABLE 3

| Dentifrice composition component | Comparative Example 3 | Example 10 | Example 11 | Example 12 | Comparative Example 4 |
|---|---|---|---|---|---|
| Anethole/l-menthol | 1:20 | 1:9 | 5:5 | 8:2 | 9:1 |
| Silicic anhydride | 20% | 20% | 20% | 20% | 20% |
| Glycerin | 30 | 30 | 30 | 30 | 20 |
| Sorbitol | 20 | 20 | 20 | 20 | 20 |
| Sodium carboxymethyl cellulose | 1.0 | 1.0 | 1.0 | 1.0 | 1.0 |
| Sodium lauryl sulfate | 1.2 | 1.2 | 1.2 | 1.2 | 1.2 |
| Lauroyl diethanolamide | 1.0 | 1.0 | 1.0 | 1.0 | 1.0 |
| Gelatin | 1.0 | 1.0 | 1.0 | 1.0 | 1.0 |
| Anethole | 0.05 | 0.1 | 0.5 | 0.4 | 0.45 |
| l-menthol | 1.0 | 0.9 | 0.5 | 0.1 | 0.05 |
| Saccharin | 0.1 | 0.1 | 1.0 | 1.0 | 1.0 |
| Orange oil | 0.05 | 0.05 | 0.05 | 0.05 | 0.05 |
| Benzaldehyde | 0.02 | 0.02 | 0.02 | 0.02 | 0.02 |
| Tranexamic acid | 0.05 | 0.05 | 0.05 | 0.05 | 0.05 |
| Anti-Pg fimbriae rabbit serum antibody | 0.2 | 0.2 | 0.2 | 0.2 | 0.2 |
| Water | balance | balance | balance | balance | balance |
| Total | 100.00 | 100.00 | 100.00 | 100.00 | 100.00 |
| Antibody retentivity (40° C./1 month storage) | Δ | ○ | ○ | ○ | Δ |
| Feel on use | X | ○ | ○ | ○ | V |

Antibody retentivity evaluation criterion

○; retentivity 70% or more

Δ: retentivity 30% to less than 70%

X: retentivity less than 30%

Feel on use evaluation criterion

○: pleasant

X: monotonous flavor, unpleasant feel

V: short refreshing, unpleasant feel

TABLE 4

| Dentifrice composition component | Example 13 | Example 14 | Example 15 | Example 16 | Example 17 | Example 18 |
|---|---|---|---|---|---|---|
| Silicic anhydride | 20% | 20% | 20% | 20% | 20% | 20% |
| Glycerin | 30 | 30 | 30 | 30 | 30 | 30 |
| Sorbitol | 20 | 20 | 20 | 20 | 20 | 20 |

TABLE 4-continued

| Dentifrice composition component | Example 13 | Example 14 | Example 15 | Example 16 | Example 17 | Example 18 |
|---|---|---|---|---|---|---|
| Sodium carboxymethyl cellulose | 1.0 | 1.0 | 1.0 | 1.0 | 1.0 | 1.0 |
| Sodium lauryl sulfate | 1.2 | 1.2 | 1.2 | 1.2 | 1.2 | 1.2 |
| Lauroyl diethanolamide | 1.0 | 1.0 | 1.0 | 1.0 | 1.0 | 1.0 |
| Gelatin | 1.0 | 1.0 | 1.0 | 1.0 | 1.0 | 1.0 |
| Carvone | 0.4 | — | — | — | — | — |
| Cineole | — | 0.3 | — | — | — | — |
| Methyl salicylate | — | — | 0.5 | — | — | — |
| Eugenol | — | — | — | 0.1 | — | — |
| Ethyl butyrate | — | — | — | — | 0.1 | — |
| Cinnamic aldehyde | — | — | — | — | — | 0.3 |
| l-menthol | 0.5 | 0.5 | 0.5 | 0.5 | 0.5 | 0.5 |
| Saccharin | 0.1 | 0.1 | 0.1 | 0.1 | 0.1 | 0.1 |
| Orange oil | 0.05 | 0.05 | 0.05 | 0.05 | 0.05 | 0.05 |
| Benzaldehyde | 0.02 | 0.02 | 0.02 | 0.02 | 0.02 | 0.02 |
| Sodium fluoride | 0.05 | 0.05 | 0.05 | 0.05 | 0.05 | 0.05 |
| Anti-Pg fimbriae rabbit serum antibody | 0.2 | 0.2 | 0.2 | 0.2 | 0.2 | 0.2 |
| Water | balance | balance | balance | balance | balance | balance |
| Total | 100.00 | 100.00 | 100.00 | 100.00 | 100.00 | 100.00 |
| Antibody retentivity (40° C./1 month storage) | ○ | ○ | ○ | ○ | ○ | ○ |
| Feel on use | ○ | ○ | ○ | ○ | ○ | ○ |

Example 19: Dentifrice

| | |
|---|---|
| Calcium hydrogen phosphate dihydride | 50.0% |
| Sorbitol | 10.0 |
| Glycerin | 10.0 |
| Carrageenan | 1.0 |
| Sodium lauryl sulfate | 1.0 |
| l-menthol | 0.3 |
| Peppermint oil | 0.6 |
| Eugenol | 0.03 |
| Anethole | 0.17 |
| Saccharin | 0.1 |
| Ethanol | 2.0 |
| Dextranase | 0.02 |
| Anti-PAC goat milk antibody or anti-Pg surface layer polysaccharide sheep serum antibody | 0.2 |
| Water | balance |
| | 100.0% |

Example 20: Dentifrice

| | |
|---|---|
| Silicic anhydride | 30.0% |
| Glycerin | 30.0 |
| Sorbitol | 20.0 |
| Carboxymethyl cellulose | 1.0 |
| Sodium lauryl sulfate | 1.2 |
| l-menthol | 0.1 |
| Carvone | 0.05 |
| Spearmint oil | 0.4 |
| Peppermint oil | 0.3 |
| Saccharin | 0.1 |
| Ethanol | 2.0 |
| Sodium fluoride | 0.1 |
| Anti-PAC horse serum antibody or anti-Pg whole cell horse serum antibody | 0.1 |
| Water | balance |
| | 100.0% |

Example 21: Dentifrice

| | |
|---|---|
| Aluminum hydroxide | 45.0% |
| Sorbitol | 20.0 |
| Carrageenan | 0.5 |
| Carboxymethyl cellulose | 1.0 |
| Lauryl diethanolamide | 1.0 |
| Sucrose monolaurate | 2.0 |
| l-menthol | 0.6 |
| Peppermint oil | 0.2 |
| Cineole | 0.4 |
| Saccharin | 0.1 |
| Anti-PAc cow milk antibody | 0.3 |
| Water | balance |
| | 100.0% |

Example 22: Dentifrice

| | |
|---|---|
| Aluminum hydroxide | 45.0% |
| Sorbitol | 20.0 |
| Carrageenan | 0.5 |
| Carboxymethyl cellulose | 1.0 |
| Lauryl diethanolamide | 1.0 |
| Sucrose monolaurate | 2.0 |
| l-menthol | 0.6 |
| Peppermint oil | 0.2 |
| Cineole | 0.4 |
| Saccharin | 0.1 |
| Anti-Pg fimbriae horse serum antibody | 0.2 |
| Anti-Aa fimbriae horse serum antibody | 0.2 |
| Water | balance |
| | 100.0% |

Example 23: Dentifrice

| | |
|---|---|
| Calcium hydrogen phosphate | 45.0% |
| Carboxymethyl cellulose | 1.0 |
| Carrageenan | 0.5 |
| Sorbitol | 35.0 |
| Propylene glycol | 3.0 |
| Sodium N-lauroylmethyltaurine | 0.5 |
| Gelatin | 1.0 |
| Ethyl p-hydroxybenzoate | 0.2 |
| Saccharin sodium | 0.1 |
| l-menthol | 0.6 |
| Methyl salicylate | 0.3 |
| Sodium monofluorophosphate | 0.7 |
| Anti-PAC hen egg antibody or anti-Av fimbriae egg antibody | 0.4 |
| Water | balance |
| | 100.0% |

Example 24: Dentifrice

| | |
|---|---|
| Aluminum hydroxide | 40.0% |
| Sodium carboxymethyl cellulose | 1.0 |
| Carrageenan | 0.5 |
| Sorbitol | 35.0 |
| Propylene glycol | 3.0 |
| Sodium N-myristoylmethyltaurine | 0.5 |
| Peptide | 1.0 |
| Methyl p-hydroxybenzoate | 0.2 |
| Saccharin sodium | 0.1 |
| l-menthol | 0.5 |
| Peppermint oil | 0.2 |
| Cinnamic aldehyde | 0.15 |
| Spice mix flavor | 0.05 |
| Anti-PAC sheep serum antibody or anti-Pi surface layer of polysaccharide sheep serum antibody | 0.5 |
| Water | balance |
| | 100.0% |

Example 25: Dentifrice

| | |
|---|---|
| Silicic anhydride | 20.0% |

-continued

| | |
|---|---|
| Sodium carboxymethyl cellulose | 1.0 |
| Sorbitol | 50.0 |
| Polyethylene glycol | 5.0 |
| Sodium N-palmitoylmethyltaurine | 0.5 |
| Casein | 1.0 |
| Sodium p-hydroxybenzoate | 0.2 |
| Saccharin sodium | 0.1 |
| l-menthol | 0.3 |
| Cineole | 0.1 |
| Ethyl butyrate | 0.01 |
| Sodium fluoride | 0.2 |
| Anti-GTF hen egg antibody | 0.3 |
| Water | balance |
| | 100.0% |

Example 26: Dentifrice

| | |
|---|---|
| Silicic anhydride | 20.0% |
| Sodium carboxymethyl cellulose | 1.0 |
| Sorbitol | 50.0 |
| Polyethylene glycol | 5.0 |
| Sodium N-palmitoylmethyltaurine | 0.5 |
| Casein | 1.0 |
| Sodium p-hydroxybenzoate | 0.2 |
| Saccharin sodium | 0.1 |
| l-menthol | 0.3 |
| Cineole | 0.1 |
| Ethyl butyrate | 0.01 |
| Tranexamic acid | 0.1 |
| Anti-Fn whole cell hen egg antibody | 0.3 |
| Water | balance |
| | 100.0% |

Example 27: Mouthwash

| | |
|---|---|
| Ethanol | 20.0% |
| l-menthol | 0.2 |
| Peppermint oil | 0.2 |
| Eugenol | 0.1 |
| Cineole | 0.05 |
| Anethole | 0.03 |
| Saccharin | 0.05 |
| Lauryl diethanolamide | 0.3 |
| Chlorohexidine gluconate | 0.01 |
| Anti-GTF horse serum antibody or anti-Cr surface layer polysaccharide goat serum antibody | 0.1 |
| Water | balance |
| | 100.0% |

Example 28: Mouthwash

| | |
|---|---|
| Sorbitol | 10.0% |
| Ethanol | 20.0 |
| Sodium N-myristoyltaurine | 0.5 |
| Sucrose stearate | 1.0 |
| Peptide | 0.5 |
| Methyl p-hydroxybenzoate | 0.1 |
| Stevioside | 0.1 |
| l-menthol | 0.2 |
| Methyl salicylate | 0.3 |
| Cinnamic aldehyde | 0.1 |
| Ethyl butyrate | 0.05 |
| Dextranase | 0.2 |
| Sodium fluoride | 0.2 |
| Anti-Aa surface layer polysaccharide hen egg antibody | 0.2 |
| Water | balance |
| | 100.0% |

Example 29: Mouthwash

| | |
|---|---|
| Sorbitol | 10.0% |
| Ethanol | 20.0 |
| Sodium N-myristoyltaurine | 0.5 |
| Sucrose stearate | 1.0 |
| Peptide | 0.5 |
| Methyl p-hydroxybenzoate | 0.1 |
| Stevioside | 0.1 |
| l-menthol | 0.2 |
| Methyl salicylate | 0.3 |
| Cinnamic aldehyde | 0.1 |
| Ethyl butyrate | 0.05 |
| Dextranase | 0.2 |
| Cetyl pyridinium chloride | 0.05 |
| Anti-Bf whole cell hen egg antibody | 0.2 |
| Water | balance |
| | 100.0% |

Example 30: Mouthwash

| | |
|---|---|
| Sorbitol | 10.0% |
| Ethanol | 20.0 |
| Sodium N-stearoylmethyltaurine | 0.5 |
| POE (20) sorbitan monooleate | 1.0 |
| Collagen | 0.5 |
| Methyl p-hydroxybenzoate | 0.1 |
| Saccharin sodium | 0.1 |
| l-menthol | 0.05 |
| Carvone | 0.1 |
| Spearmint oil | 0.3 |
| Peppermint oil | 0.3 |
| Anti-PAC cow milk antibody or anti-Td surface layer polysaccharide cow milk antibody | 0.4 |
| Water | balance |
| | 100.0% |

Example 31: Tablet

| | |
|---|---|
| Gum arabic | 6.0% |
| Glucose | 72.0 |
| Gelatin | 3.0 |
| l-menthol | 0.2 |
| Cineole | 0.1 |
| Benzaldehyde | 0.05 |
| Sodium ascorbate | 0.1 |
| Anti-PAc goat milk antibody or anti-Aa capsule goat milk antibody | 0.1 |
| Water | balance |
| | 100.0% |

Example 32: Chewing gum

| | |
|---|---|
| Gum base | 43.9% |
| Calcium carbonate | 2.0 |
| Hydrolyzed starch | 15.0 |
| Sugar | 29.0 |
| Sucrose palmitate | 1.0 |
| Fructose | 4.0 |
| Aldose | 3.0 |
| l-menthol | 0.6 |
| Carvone | 0.4 |
| Fruit mix flavor | 1.0 |
| Anti-PAc hen egg antibody or anti-Pg fimbriae hen egg antibody | 0.1 |
| Water | balance |
| | 100.0% |

We claim:

1. An oral composition characterized in that a flavor component selected from the group consisting of cineole, methyl salicylate, ethyl butyrate, and cinnamic aldehyde, and l-menthol are blended in a weight ratio of from 1:9 to 8:2 in an oral composition containing an antibody selected from the group consisting of a serum antibody, egg yolk antibody and milk antibody.

2. The oral composition of claim 1 wherein said antibody is an antibody specific for dental cariogenic bacteria.

3. The oral composition of claim 2 wherein said cariogenic bacteria is *Streptococcus mutans*.

4. The oral composition of claim 1 wherein said antibody is an antibody specific for periodontal disease associated bacteria.

5. The oral composition of claim 4 wherein said periodontal disease associated bacteria is selected from the group consisting of *Actinobacillus actinomycetemcomitans, Porphyromonas gingivalis, Actinomyces viscosus, Prevotella intermedia, Fusobacterium nucleatum*, species of Capnocytophaga, *Campylobacter rectus, Bacteroides forsythus*, and Spirochaeta such as *Treponema denticola*.

6. An oral composition according to claim 1, wherein the flavor component and the l-menthol are blended in a weight ratio of from 2:8 to 7:3.

7. An oral composition according to claim 1, wherein the flavor component is cineole.

8. An oral composition according to claim 1, wherein the flavor component is methyl salicylate.

9. An oral composition according to claim 1, wherein the flavor component is ethyl butyrate.

10. An oral composition according to claim 1, wherein the flavor component is cinnamic aldehyde.

* * * * *